United States Patent
Holmgren et al.

(10) Patent No.: US 7,671,211 B1
(45) Date of Patent: Mar. 2, 2010

(54) SUBSTRATES FOR THIOREDOXIN REDUCTASE

(75) Inventors: Arne Holmgren, c/o Medical Nobel Institute for Biochemistry, Karolinska Institute, S-17177 Stockholm (SE); Marjan H. Amiri, Stockholm (SE); Hiroyuki Masayasu, Tokyo (JP)

(73) Assignee: Arne Holmgren, Stockholm (SE)

( * ) Notice: Subject to any disclaimer, the term of this patent is extended or adjusted under 35 U.S.C. 154(b) by 424 days.

(21) Appl. No.: 09/926,218

(22) PCT Filed: Mar. 31, 2000

(86) PCT No.: PCT/JP00/02076

§ 371 (c)(1),
(2), (4) Date: Jan. 28, 2002

(87) PCT Pub. No.: WO00/58281

PCT Pub. Date: Oct. 5, 2000

(30) Foreign Application Priority Data

Mar. 31, 1999 (JP) .................................. 11-092789
Apr. 8, 1999 (JP) .................................. 11-101478

(51) Int. Cl.
C07D 293/00 (2006.01)
(52) U.S. Cl. ........................ 548/121; 562/899; 514/183
(58) Field of Classification Search ................. 562/899; 548/121; 514/183
See application file for complete search history.

(56) References Cited

U.S. PATENT DOCUMENTS

| | | | |
|---|---|---|---|
| 4,352,799 A | 10/1982 | Renson et al. | |
| 4,418,069 A * | 11/1983 | Welter et al. ................. | 514/359 |
| 4,454,068 A | 6/1984 | Welter et al. | |
| 4,550,168 A | 10/1985 | Welter et al. | |
| 4,618,669 A | 10/1986 | Dereu et al. | |
| 4,711,961 A | 12/1987 | Welter et al. | |
| 4,730,053 A | 3/1988 | Dereu et al. | |
| 4,757,063 A | 7/1988 | Parnham | |
| 4,774,252 A | 9/1988 | Welter et al. | |
| 4,784,994 A | 11/1988 | Romer et al. | |
| 4,873,350 A | 10/1989 | Welter et al. | |
| 4,910,313 A | 3/1990 | Welter et al. | |
| 5,021,242 A | 6/1991 | Romer et al. | |
| 5,480,888 A | 1/1996 | Kodama et al. | |
| 6,335,036 B1 | 1/2002 | Nakagami et al. | |
| 2004/0029934 A1 | 2/2004 | Ebihara et al. | |
| 2004/0053888 A1 | 3/2004 | Suzuki et al. | |

FOREIGN PATENT DOCUMENTS

| | | |
|---|---|---|
| AU | 199721497 | 8/1997 |
| CA | 2276984 | 1/2000 |
| DE | 36 38 124 A1 | 5/1988 |
| EP | 0366990 | 5/1990 |
| EP | 0826370 A1 | 3/1997 |
| JP | 57-56427 | 4/1982 |
| JP | 59-39894 | 3/1984 |
| JP | 59-42373 | 3/1984 |
| JP | 60-226868 | 11/1985 |
| JP | 61-50963 | 3/1986 |
| JP | 61-137856 | 6/1986 |
| JP | 61-254578 | 11/1986 |
| JP | 61-275264 | 12/1986 |
| JP | 62-294613 | 12/1987 |
| JP | 63-5022 | 1/1988 |

(Continued)

OTHER PUBLICATIONS

Bjornstedt et al, Journal of Biological chemistry, vol. 270, No. 20, pp. 11761-11764.*

(Continued)

*Primary Examiner*—Daniel M Sullivan
*Assistant Examiner*—Sudhakar Katakam
(74) *Attorney, Agent, or Firm*—Greenblum & Bernstein, P.L.C.

(57) ABSTRACT

A substrate for thioredoxin reductase which comprises a compound represented by the following general formula (I) or (I'):

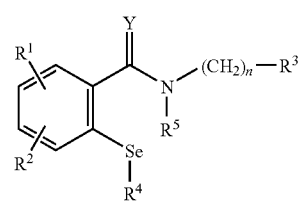

(1)

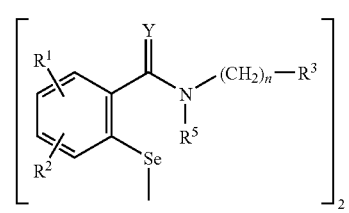

(1')

wherein $R^1$ and $R^2$ independently represent a hydrogen atom, a halogen atom, a trifluoromethyl group and the like; $R^3$ represents an aryl group, an aromatic heterocyclic group and the like; $R^4$ represents a hydrogen atom, a hydroxyl group, a —S-α-amino acid group and the like; $R^5$ represents a hydrogen atom or a $C_1$-$C_6$ alkyl group; Y represents oxygen atom or sulfur atom; n represents an integer of from 0 to 5; and the selenium atom may be oxidized, whose example includes 2-phenyl-1,2-benzisoselenazol-3(2H)-one or a ring-opened form thereof. The substrate is reduced by thioredoxin reductase in the presence of NADPH and enhances peroxidase activity of thioredoxin reductase.

10 Claims, 8 Drawing Sheets

FOREIGN PATENT DOCUMENTS

| JP | 63-27431 | 2/1988 |
|---|---|---|
| JP | 63-79875 | 4/1988 |
| JP | 63-183528 | 7/1988 |
| JP | 64-56615 | 3/1989 |
| JP | 1-100125 | 4/1989 |
| JP | 1-131113 | 5/1989 |
| JP | 1-131114 | 5/1989 |
| JP | 1-132522 | 5/1989 |
| JP | 1-135718 | 5/1989 |
| JP | 1-180825 | 7/1989 |
| JP | 1-294622 | 11/1989 |
| JP | 2-83321 | 3/1990 |
| JP | 2-38591 | 8/1990 |
| JP | 2-250876 | 10/1990 |
| JP | 5-255084 | 10/1993 |
| JP | 5-310570 | 11/1993 |
| JP | 7-233056 | 9/1995 |
| JP | 9-263533 | 10/1997 |
| JP | 2000-16935 | 1/2000 |
| JP | 2000-86508 | 3/2000 |
| JP | 2000-256335 | 9/2000 |
| JP | 2000-344663 | 12/2000 |
| JP | 2001-261555 | 9/2001 |
| WO | 96/33712 | 10/1996 |
| WO | 98/29417 A1 | 7/1998 |
| WO | 02/053154 | 7/2002 |
| WO | 02/055076 | 7/2002 |

OTHER PUBLICATIONS

Kumar et al, Eur. J. Biochem., vol. 207, 1992, pp. 435-439.*
English Language Abstract of JP 7-233056.
Armin Muller et al., "A Novel Biologically Active Seleno-Organic Compound-I: Gluthathione. Peroxidase-Like Activity in Vitro and Antioxidant Capacity of PZ 51 (Ebselen)", *Biochemical. Pharmacology*, vol. 33, No. 20, pp. 3235-3239 (1984).
Mark P. Mattson et al., "Amyloid Ox-Tox Transducers", *Nature*, vol. 382, pp. 674-675 (1996).
David M. Hockenbery et al., "Bcl-2 Functions in an Antioxidant Pathway to Prevent Apoptosis", *Cell*, vol. 75, pp. 241-251 (1993).
Frank J.T. Staal et al., "Intracellular Thiols Regulate Activation of Nuclear Factor κB and Transcription of Human Immunodeficiency Virus", *Proc. Natl. Acad. Sci. USA*, vol. 87, pp. 9943-9947 (1990).
Takuma Hayashi et al., "Oxidoreductive Regulation of Nuclear Factor κB: Involvement of A Cellular Reducing Catalyst Thioredoxin", *The Journal of Biological Chemistry*, vol. 268, No. 15, pp. 11380-11388 (1993).
Gavin E. Arteel et al., "Function of Thioredoxin Reductase as a Peroxynitrite Reductase Using Selenocystine or Ebselen", *Chem. Res. ZToxicol.*, vol. 12, No. 3, pp. 264-269 (1999).
Engman et al., "Diaryl chalcogenides as selective inhibitors of thioredoxin reductase and potential antitumor agents", Anticancer Res., Nov.-Dec. 1997;17(6D):4599-605 (Abstract).
Klotz et al., "Defenses against peroxynitrite: selenocompounds and flavonoids", Toxicol Lett., Apr. 11, 2003;140-141:125-32 (Abstract).
Zhao et al., "A novel antioxidant mechanism of ebselen involving ebselen diselenide, a substrate of mammalian thoredoxin and thioredoxin reductase", J Biol Chem. Oct. 18, 2002;277(42):39456-62.
Zhao et al., "Ebselen: A substrate for human thioredoxin reductase strongly stimulating its hydroperoxide reductase activity and a superfast thioredoxin oxidant", Proc Natl Acad Sci U S A. Jun. 25, 2000; 99(13):8579-84.
Holmgren et al., "Antioxidant function of thioredoxin and glutaredoxin systems", Antioxid Redox Signal. 2000 Winter;2(4):811-20 (Abstract).
Sies et al., "Interaction of peroxynitrite with selenoproteins and glutathione peroxidase mimics", Free Radic Biol Med. May 15, 2000;28(10):1451-5 (Abstract).
Arteel et al., "Function of thioredoxin reductase as a peroxynitrite reductase using selenocystine or ebselen", Chem Res Toxicol. Mar. 1999;12(3):264-9 (Abstract).
English language Abstract of JP 61-50963, published Mar. 18, 1986.
English language Abstract of JP 63-183528, published Jul. 28, 1988.
English language Abstract of JP 63-27431, published May 2, 1988.
English language Abstract of JP 64-56615, published Mar. 3, 1989.
English language Abstract of JP 1-131113, published May 24, 1989.
English language Abstract of JP 1-131114, published May 24, 1989.
English language Abstract of JP 1-132522, published May 25, 1981.
English language Abstract of JP 1-135718, published May 29, 1989.
English language Abstract of JP 1-180825, published Jul. 18, 1989.
English language Abstract of JP 1-294622, published Nov. 28, 1989.
English language Abstract of JP 2-83321, published Mar. 23, 1990.
English language Abstract of JP 2000-86508, published Mar. 28, 2000.
English language Abstract of JP 2000-256335, published Sep. 19, 2000.
English language Abstract of JP 2000-344663, published Dec. 12, 2000.
English language Abstract of JP 2001-261555, published Sep. 26, 2001.
Holmgren A., Thioredoxin, Ann. Rev. Biochem., 54:237-271, 1985.
Schewe, T., Gen. Pharmacol. 26, vol. 26, No. 6, 1153-1169, 1995.
A lecture by Arne Holmgren at a conference at the Pasteur Institute disclosing the results that mammalian thioredoxin reductase was a selenoprotein with a selenocysteine residue in the active site, which was later published in Oxidative Stress, in Cancer, AIDS and Neurodegenerative Diseases (Montagnier, Olivier, Pasquier, Eds.) Marcel Dekker, Inc., New York, pp. 229-246, 1998, "23 Redox Regulation by the Thioredoxin and Glutaredoxin Systems", Holmgren et al.
Engman et al., "Diaryl Chalcogenides as Selective Inhibitors of Thioredoxin Reductase and Potential Antitumor Agents", Anticancer Research, Helenic Anticancer Institute, Anthens, GR, vol. 17, No. 6D, 1997, pp. 4599-4605.
Parnham M.J., "The Pharmaceutical Potential of Seleno Organic Compounds" Expert Opinion on Investigational Drugs, Ashley Publications Ltd., GB, vol. 5, No. 7, 1 Jul. 1996, pp. 861-870, XP000645626 ISSN: 1354-3784.
Database Biosis [Online] Biosciences Information Service, Philadelphia, PA, US; Sep. 1998, Squadrito Giuseppe L. et al., "Oxidative chemistry of nitric oxide: The roles of superoxide, peroxynitrite, and carbon dioxide" Database Accession No. PREV1 99800442902; & Free Radical Biology and Medicine, vol. 25, No. 4-5, Sep. 1998, pp. 392-493, ISSN: 0891-5849.
Wendel A. et al., "A novel biologically active seleno-organic compound-VI -Protection by ebselen (PZ 51) against galactosamine/endotoxin-induced hepatitis in mice" Biochemical Pharmacology, Pergamon, Oxford, GB, vol. 35, No. 13, Jul. 1, 1986, pp. 2115-2118, XP0238481 94 ISSN: 0006-2952 [retrieved on Jul. 1, 1986].

* cited by examiner

SUBSTRATES FOR THIOREDOXIN REDUCTASE

TECHNICAL FIELD

The present invention relates to a substrate for thioredoxin reductase, and an enhancer of peroxidase activity of thioredoxin reductase.

BACKGROUND ART

The existence of the thioredoxin (hereinafter abbreviated as "TRX" in the specification)/thioredoxin reductase system is known as one of the reduction-oxidation pathway of thiol group. The system regulates reversible reduction-oxidation reaction of thiol group and maintains a constant thiol level in vivo so as to prevent functional depression of thiol protein by formation of disulfide bonds and advancement of peroxidation state.

It has been elucidated that thioredoxin reductase has activity of reductively cleaving a disulfide bond of a target protein in the presence of NADPH and thioredoxin, as well as a variety of other physiological activities. Thioredoxin, a substrate for thioredoxin reductase, is a protein containing two thiol groups in the molecule, and functions also as a hydrogen donor in reduction of ribonucleotide by ribonucleotide reductase.

DISCLOSURE OF THE INVENTION

An object of the present invention is to provide substances which function as a substrate for thioredoxin reductase and can activate the thioredoxin/thioredoxin reductase system. In particular, the object is to provide a substance which can enhance peroxidase activity proceeded by thioredoxin reductase.

The inventors of the present invention conducted intensive studies to achieve the foregoing object. As a result, they found that selenium compounds such as 2-phenyl-1,2-benzisoselenazol-3(2H)-one can function as substrates of thioredoxin reductase by repeated self reduction-oxidation similarly to thioredoxin in the thioredoxin/thioredoxin reductase system, and that the compounds can remarkably enhance peroxidase activity of thioredoxin reductase in the presence of thioredoxin reductase and thioredoxin. The present invention was achieved on the basis of these findings. It is known that the aforementioned substances can reduce a peroxide (active oxygen) by glutathione peroxidase-like activity (Muller, A. et al., Biochem. Pharmacol., 33, pp.3235-3239). However, the reduction of a peroxide by glutathione peroxidase is based on totally different mechanism from that proceeded by thioredoxin reductase.

The present invention thus provides a substrate for thioredoxin reductase which comprises a substance selected from the group consisting of a compound represented by the following general formula (1) or (1') and a physiologically acceptable salt thereof, and a hydrate thereof and a solvate thereof:

wherein $R^1$ and $R^2$ independently represent a hydrogen atom, a halogen atom, a trifluoromethyl group, a nitro group, a $C_1$-$C_6$ alkyl group, or a $C_1$-$C_6$ alkoxyl group, or $R^1$ and $R^2$ may combine together to represent methylenedioxy group; $R^3$ represents an aryl group, an aromatic heterocyclic group, a 5- to 7-membered cycloalkyl group, or a 5- to 7-membered cycloalkenyl group, and the aryl group, the aromatic heterocyclic group, the cycloalkyl group and the cycloalkenyl group may be substituted with one or more substituents; $R^4$ represents a hydrogen atom, a hydroxyl group, a —S-glutathione group, a —S-α-amino acid group, or an aralkyl group whose aryl moiety may be substituted with one or more substituents; $R^5$ represents a hydrogen atom or a $C_1$-$C_6$ alkyl group, or $R^4$ and $R^5$ may combine together to represent single bond; Y represents oxygen atom or sulfur atom; n represents an integer of from 0 to 5; and the selenium atom may be oxidized.

According to preferred embodiments of the aforementioned invention, there are provided the substrate for thioredoxin reductase which comprises a substance selected from the group consisting of 2-phenyl-1,2-benzisoselenazol-3(2H)-one or a ring-opened form thereof and a physiologically acceptable salt thereof, and a hydrate thereof and a solvate thereof; and the substrate for thioredoxin reductase which are reduced by thioredoxin reductase in the presence of NADPH.

According to another aspect, there is provided an enhancer of peroxidase activity of thioredoxin reductase which comprise a substance selected from the group consisting of a compound represented by the aforementioned general formula (I) or (I') and a physiologically acceptable salt thereof, and a hydrate thereof and a solvate thereof. As a preferred embodiment of the aforementioned invention, there is provided the enhancer which comprises a substance selected from the group consisting of 2-phenyl-1,2-benzisoselenazol-3(2H)-one or a ring-opened form thereof and a physiologically acceptable salt thereof, and a hydrate thereof and a solvate thereof.

According to further aspects of the present invention, there are provided a catalyst comprising a substance selected from the group consisting of a compound represented by the aforementioned general formula (I) or (I') and a physiologically acceptable salt thereof, and a hydrate thereof and a solvate thereof which oxidizes reduced thioredoxin in the peroxidase reaction of thioredoxin reductase; a reducing agent comprising the aforementioned substance which reduces a peroxide by oxidizing reduced thioredoxin in the peroxidase reaction of thioredoxin reductase; and an antioxidant comprising the aforementioned substance which prevents peroxidation of a substance in vivo by oxidizing reduced thioredoxin in the peroxidase reaction of thioredoxin reductase.

There are also provided a use of a substance selected from the group consisting of a compound represented by the aforementioned general formula (I) or (I') and a physiologically acceptable salt thereof, and a hydrate thereof and a solvate thereof as the aforementioned substrate, as the aforementioned enhancer of peroxidase activity of thioredoxin reductase, as the aforementioned catalyst, as the aforementioned reducing agent, and as the aforementioned antioxidant; a use of a substance selected from the group consisting of a compound represented by the aforementioned general formula (I) or (I') and a physiologically acceptable salt thereof, and a hydrate thereof and a solvate thereof for the manufacture of the aforementioned substrate, the aforementioned enhancer of peroxidase activity of thioredoxin reductase, the aforementioned catalyst, the aforementioned reducing agent, or the aforementioned antioxidant.

In addition to these inventions, there are provided a method for enhancing peroxidase activity of thioredoxin reductase in vivo which comprises the step of administering an effective amount of a substance selected from the group consisting of a compound represented by the aforementioned general formula (I) or (I') and a physiologically acceptable salt thereof, and a hydrate thereof and a solvate thereof to a mammal including a human; a method for reducing a peroxide in vivo which comprises the step of administering an effective amount of the aforementioned substance to a mammal including a human; and a method for preventing peroxidation of a substance in vivo which comprises the step of administering an effective amount of the aforementioned substance to a mammal including a human.

BEST MODE OF CARRYING OUT THE INVENTION

As the $C_1$-$C_6$ alkyl group represented by $R^1$ and $R^2$, either a straight or a branched chain alkyl group may be used, and examples include methyl group, ethyl group, n-propyl group, isopropyl group, cyclopropyl group, n-butyl group, sec-butyl group, isobutyl group, tert-butyl group, n-pentyl group, and n-hexyl group. As the $C_1$-$C_6$ alkoxyl group represented by $R^1$ and $R^2$, either a straight or a branched chain alkoxyl group may be used, and examples include methoxy group, ethoxy group, n-propoxy group, isopropoxy group, n-butoxy group, sec-butoxy group, tert-butoxy group, n-pentoxy group, and n-hexoxy group.

As the aryl group represented by $R^3$, for example, a monocyclic to a tricyclic, preferably a monocyclic or a bicyclic aryl group having 6 to 14 carbon atoms, preferably 6 to 10 carbon atoms can be used. More specifically, phenyl group or naphthyl group and the like are preferred. As the aromatic heterocyclic group represented by $R^3$, for example, a monocyclic to a tricyclic, preferably a monocyclic or a bicyclic aromatic heterocyclic group containing one ore more heteroatoms such as nitrogen atom, oxygen atom and sulfur atom can be used. When two or more heteroatoms are contained, they may be same or different. Examples include thienyl group, furyl group, pyrrolyl group, imidazolyl group, pyrazolyl group, isoxazolyl group, pyridyl group, pyrazinyl group, pyrimidinyl group, pyridazinyl group, indolizinyl group, isoindolyl group, indolyl group, isoquinolyl group, quinolyl group, phthalazinyl group, naphthylidinyl group, quinoxalinyl group, quinazolinyl group, cinnolinyl group, pteridinyl group, carbazolyl group, acridinyl group, phenanthridinyl group, and phenothiazinyl group.

The aryl group, the aromatic heterocyclic group, the 5- to 7-membered cycloalkyl group, or the 5- to 7-membered cycloalkenyl group represented by $R^3$ may have one or more substituents on the ring. When the ring is substituted with two or more substituents, they may be same or different. The position of the substituent is not particularly limited, and the substituent may be present at any position on the ring. The type of the substituent is not particularly limited, and examples include a $C_1$-$C_6$ alkyl group, a $C_2$-$C_6$ alkenyl group, a $C_2$-$C_6$ alkynyl group, a $C_6$-$C_{14}$ aryl group, a heterocyclic group (the heterocycle used herein includes aromatic heterocyclic groups and partially saturated or saturated heterocyclic groups), a halogen atom (the halogen atom used herein may be any one of fluorine atom, chlorine atom, bromine atom, or iodine atom), hydroxyl group, oxo group, amino group, ammonium group, imino group, mercapto group, thioxo group, cyano group, nitro group, carboxyl group, phosphate group, sulfo group, hydrazino group, a $C_1$-$C_6$ ureido group, a $C_1$-$C_6$ imido group, isothiocyanate group, isocyanate group, a $C_1$-$C_6$ alkoxyl group, a $C_1$-$C_6$ alkylthio group, a $C_6$-$C_{14}$ aryloxy group, a heterocyclic-oxy group, a $C_6$-$C_{14}$ arylthio group, a heterocyclic-thio group, a $C_7$-$C_{15}$ aralkyl group, a heterocycle-alkyl group, a $C_7$-$C_{15}$ aralkyloxy group, a heterocyclic-alkyloxy group, a $C_1$-$C_6$ alkoxycarbonyl group, a $C_6$-$C_{14}$ aryloxycarbonyl group, a heterocyclic-oxycarbonyl group, a $C_2$-$C_7$ alkylcarbonyl group, a $C_6$-$C_{14}$ arylcarbonyl group, a heterocyclic-carbonyl group, a $C_2$-$C_7$ alkylcarbonyloxy group, a $C_6$-$C_{14}$ arylcarbonyloxy group, a heterocyclic-carbonyl oxygroup, a $C_2$-$C_8$ alkylcarbonylamino group, a $C_1$-$C_6$ sulfonyl group, a $C_1$-$C_6$ sulfinyl group, a $C_1$-$C_6$ sulfonylamino group, a $C_1$-$C_6$ carbamoyl group, and a $C_2$-$C_6$ sulfamoyl group.

The substituents exemplified above may be further substituted with one or more other substituents. Examples of such substituents include a hydroxy-$C_1$-$C_6$ alkyl group, a halogenated-$C_1$-$C_6$ alkyl group, a mono- or di-$C_1$-$C_6$ alkylamino group, a halogenated-$C_1$-$C_6$ alkylcarbonyl group, a halogenated-$C_6$-$C_{14}$ aryl group, a hydroxy-$C_6$-$C_{14}$ aryl group, and a mono- or di-$C_1$-$C_6$ alkylcarbamoyl group. However, the substituents explained above are referred to only for exemplification, and the substituents used are not limited to these examples.

Although the type of the —S-α-amino acid group represented by $R^4$ is not particularly limited, the group may preferably be an amino acid residue containing thiol group. The —S-α-amino acid residue may be a residue of an amino acid which constitutes a protein or a peptide compound. The type of proteins or peptide compounds is not particularly limited so far as they are physiologically acceptable. For example, serum protein such as albumin and globulin may preferably be used. Among serum protein, albumin is more preferred, and human albumin is particularly preferred. Examples of the aralkyl group represented by $R^4$ whose aryl moiety may optionally be substituted with one or more substituents include benzyl group, parahydroxybenzyl group, and 2,4-dihydrobenzyl group. $R^4$ and $R^5$ may combine together to represent single bond, and in that case, a 5-membered ring is formed which contains the nitrogen atom bound to $R^5$ and the selenium atom. As the $C_1$-$C_6$ alkyl group represented by $R^5$, those exemplified above can be used.

As the substrate for thioredoxin reductase of the present invention, physiologically acceptable salts of the compounds represented by the aforementioned general formula (1) or (1') may be used. The physiologically acceptable salt can suitably be chosen by the person skilled in the art. Hydrates of the compounds as free form or physiologically acceptable salts may also be used. When the compound represented by the aforementioned general formula (1) or (1') has one or more asymmetric carbon atoms, stereoisomers such as optical isomers and diastereoisomers, any mixture of the stereoisomers, racemates and the like may be used as the substrates of the present invention.

Examples of the substrate of the present invention include 2-phenyl-1,2-benzisoselenazol-3(2H)-one (referred to as "ebselen" in the generic name) and S-(2-phenylcarbamoyl-phenylselenyl)albumin. Physiologically acceptable salts or hydrates of these compounds are also preferred as the substrates of the present invention. A method for the preparation of 2-phenyl-1,2-benzisoselenazol-3(2H)-one is disclosed in Japanese Patent Publication (KOKOKU) No. (Hei) 2-38591/1990, and that of S-(2-phenylcarbamoyl-phenylselenyl)albumin in Japanese Patent Unexamined Publication (KOKAI) No. (Hei) 7-233056/1995. Accordingly, by referring to these preparation methods, the person skilled in the art can easily prepare any compound falling within the scope of the aforementioned general formula (1) or (1').

The substrate of the present invention represented by the aforementioned general formula (1) or (1') is reduced by thioredoxin reductase and can enhance peroxidase activity of the thioredoxin reductase. The substrate of the present invention can also function as a catalyst which oxidizes reduced thioredoxin in the peroxidase reaction proceeded by the thioredoxin reductase, and also function as a reducing agent which reduces a peroxide by oxidizing reduced thioredoxin in the peroxidase reaction proceeded by the thioredoxin reductase. In addition, the substrate of the present invention can function as an antioxidant which prevents peroxidation of substances in vivo by oxidizing reduced thioredoxin in the peroxidase reaction proceeded by the thioredoxin reductase. Therefore, administration of the substrate of the present invention as a medicament to a mammal including a human can enhance the peroxidase reaction proceeded by the thioredoxin reductase in vivo. As a result, peroxidation of substances in vivo can be prevented or peroxides in vivo can be reduced, thereby homeostasis of oxidation-reduction state of thiol proteins and thiol compounds in vivo can be maintained. The medicament comprising the substrate of the present invention as an active ingredient is useful for the preventive and/or therapeutic treatment of diseases caused by abnormal regulation of intracellular oxidation-reduction and diseases with abnormal regulation of intracellular oxidation/reduction (Mattson, M. P. et al., Nature, 382, pp.674-675, 1996). Examples of such diseases include, for example, ischemic organ diseases (brain, heart, liver, kidney, digestive organs and the like), nerve degenerative diseases caused by inappropriate apoptosis induction (Alzheimer's disease, Parkinson's disease, Huntington's chorea, familial amyotrophic lateral sclerosis [ALS], AIDS and the like), radiation injury, malignant tumor (leukemia etc.), and various inflammatory diseases and endotoxin shock.

Although it is not intended to be bound by any specific theory, the relation between oxidation stress and ischemic organ diseases, various inflammation or endotoxin shock has been recognized, and the participation of inappropriate apoptosis induction in these ischemic organ diseases has been revealed in recent years (Hockonbery, D. M. et al., Cell, 75, pp.241-251, 1993). In the process of inducing apoptosis, it is known that generation of intracellular peroxides (active oxygen) due to various factors, particularly hydrogen peroxide, triggers the activation of intracellular nucleoprotein transcription factor NF-κB, that is, release of suppressive protein IκB from NF-κB is started and then the programmed cell death (apoptosis) is induced (Frank, J. T. et al., Proc. Natl. Acad. Sci. USA., 87, pp.9943-9947, 1990).

The NF-κB is also under reduction-oxidation control by thioredoxin (Hayashi, T. et al., Biol. Chem., 268, pp.11380-11388, 1993). Normally, SH group of NF-κB bound to IκB, i.e., in the inactivated state, forms a S—S bond and cannot be approached by thioredoxin due to hindrance of IκB. Accordingly, even if IκB is released by activation of NF-κB through stimulations, the oxidized NF-κB cannot bind to DNA. However, when thioredoxin reduces the S—S bond of the NF-κB to form NF-κB as the activated form, the activated NF-κB migrates into the nucleus and binds to DNA, and then activates genes to induce apoptosis and various inflammatory reactions. Therefore, the substrate of the present invention is expected to participate in suppression of the reduction by Trx.

When the substrate of the present invention is used as a medicament, the substance selected from the group consisting of the compound represented by the aforementioned general formula (I) or (I') and the physiologically acceptable salt thereof, and the hydrate thereof and the solvate thereof, per se, may be administered. Generally, it is preferred to prepare and administer a pharmaceutical composition containing the aforementioned substance as an active ingredient together with one or more pharmaceutical additives. As the pharmaceutical additive, for example, vehicles, binders, disintegrants, and solubilizers can be used, and two or more types of pharmaceutical additives may be used in combination. The form of the pharmaceutical composition is not particularly limited, and examples include the compositions for oral administration such as tablets, capsules, powders, granules and syrups, and those for parenteral administration such as injections, drip infusions, injections, suppositories, transdermal preparations, preparations for mucous membrane, creams, ointments, nasal drops, eye drops, ear drops and patches. These pharmaceutical compositions can be manufactured according to conventional methods in the art.

A dose of the aforementioned medicament can appropriately be chosen depending on the conditions such as the type of a disease to be treated, the age and body weight of a patient and severity of the disease. For example, in oral administration, the dose may be in the range of from 0.05 to 5,000 mg (as the amount of the active ingredient) per day for an adult. When a medicament containing 2-phenyl-1,2-benzisoselenazol-3(2H)-one as an active ingredient is used, the dose for oral administration may preferably be in the range of from 100 to 2,000 mg (as the amount of the active ingredient), more preferably in the range of from 200 to 1,000 mg per day for an adult. However, the aforementioned dose can appropriately be increased or decreased depending on the aforementioned conditions.

EXAMPLES

The present invention will be further explained with reference to examples. However, the present invention is not limited to these examples. In the following examples, compound A represents 2-phenyl-1,2-benzisoselenazol-3(2H)-one (sometimes referred to as "Ebselen" in the figures).

Example 1

Formulation Example (Tablet)

| | |
|---|---|
| Compound A | 50 mg |
| Carboxymethylcellulose | 25 mg |
| Starch | 5 mg |
| Crystalline cellulose | 40 mg |
| Magnesium stearate | 2 mg |
| Total | 122 mg |

Example 2

Experimental Example (A) Materials and Methods (1) Materials and Enzymes

NADPH and DTNB were from Sigma. Hydrogen peroxide (30%) and dimethyl sulfoxide (DMSO) were from Merck. Thioredoxin reductase (TrxR) from calf thymus or human placenta were purified to homogeneity (activity: 25 µmol of NADPH oxidized per min per mg of the enzyme) essentially as described for the rat liver enzyme. Thioredoxin (Trx) from E.coli was a homogeneous preparation and recombinant human thioredoxin and the mutant C62S/C72S were prepared as described by Ren et al. Compound A was dissolved in dimethyl sulfoxide (DMSO) before experiments.

(2) Spectrophotometric Measurements

The activity of enzyme in the presence of compound A was determined for a sample in semimicro quarts cuvettes at room temperature by using a Zeiss PMQ3 spectrophotometer equipped with an automatic sample exchanger and a recorder.

(3) Enzyme Assays

Measurements of thioredoxin reductase activity were performed in TF buffer (50 mM Tris-Cl, 1 mM EDTA, pH 7.5) with 100 µM NADPH and a given amount of Compound A. Reactions were carried out with addition of 5 or 10 µl of stock solution of thioredoxin reductase in a final volume of 0.55 ml. Cuvettes used as reference contained the same amount of DMSO as in the samples and also thioredoxin reductase. Absorbance of the control cuvette was automatically subtracted by the spectrophotometer. The reactions were followed at 340 nm.

The activity of thioredoxin reductase was determined in the insulin assay. A mixture of 100 mM potassium phosphate (pH 7.0), 2 mM NADPH, and 0.16 mM insulin was added with Compound A and thioredoxin, and then with thioredoxin reductase in a total volume of 0.55 ml for the reaction. The progress of reduction of insulin disulfides was followed at 340 nm. Generated sulfhydryl or selenol groups were measured at 412 nm by addition of 0.50 ml of a mixture of 6 M guanidine-HCl, 0.20 M Tris-Cl (pH 8.0), 1 mM DTNB and calculated using a molar extinction coefficient of 13,600 $M^{-1}cm^{-1}$. DTNB reducing activity of thioredoxin reductase by using NADPH was measured at 412 nm in 100 mM potassium phosphate (pH 7.0) containing 10 mM EDTA, 0.2 mM NADPH, 5 mM DTNB and 0.1 mg per ml of bovine serum albumin.

(4) Calculation of Selenol Groups Generated from NADPH Oxidations

Compound A absorbs at 340 nm with a 4,000 $M^{-1}cm^{-1}$ molar extinction coefficient, and N-phenyl-2-carboxamidobenzene selenol, the reduction product of selenol by a dithiol, has half the absorption (2000 $M^{-1}cm^{-1}$) at 340 nm. The formation of the compound A-selenol was confirmed by measuring absorption spectra in the presence or absence of excess DTT. In calculations of the formation of compound A-selenol, a molar extinction coefficient of 8,200 $M^{-1}cm^{-1}$ was used since oxidation of NADPH to $NADP^+$ yields 6,200 $M^{-1}cm^{-1}$.

(5) Fluorescence Measurement

Protein fluorescence was measured with a thermostated SPEX-Fluoro Max instrument. $Trx-(SH)_2$ was prepared from E.coli $Trx-S_2$ 640 µM which was incubated at room temperature for 20 min with 10 mM DTT. DTT was subsequently removed by gel chromatography (on a NAP-5 column (Pharmacia) using $N_2$ equilibrated buffer). $Trx-(SH)_2$ was mixed with Compound A dissolved in a total volume of 3 ml of a mixture (pH 7.5) of 0.1 M potassium phosphate and 1 mM EDTA, and fluorescence was immediately measured in the spectrofluorimeter at 22° C. Excitation of fluorescence was at 290 nm and emission spectra from 300 to 500 nm were recorded. Fluorescence at 340 nm was used to follow the oxidation of $Trx-(SH)_2$ to record the rate of the reaction.

(B) Results (1) Reduction of Compound A by Human Thioredoxin Reductase

Figure 1:
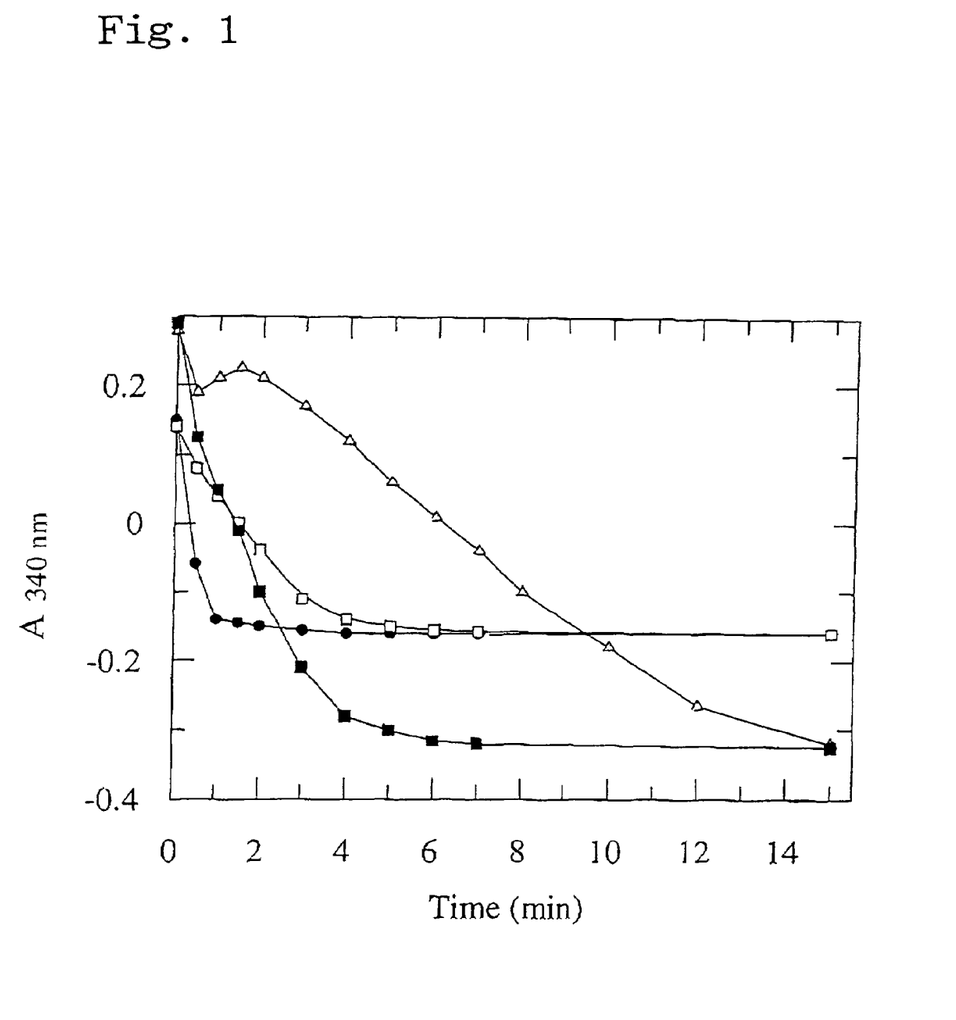
FIG. 1 shows reduction of Compound A (2-phenyl-1,2-benzisoselenazol-3(2H)-one, ebselen) by human thioredoxin reductase.

It was revealed that compound A was used as a substrate for human thioredoxin reductase because the absorbance at 340 nm decreased rapidly when the pure human thioredoxin reductase (40 nM or 4.5 µg/ml) was added to a cuvette containing 50 or 100 µM of Compound A and NADPH (100 µl). The result is shown in FIG. 1. Compound A 50 µM (●) or 100 µM (□) was dissolved in 0.55 ml of a solution containing 50 mM Tris-Cl, 1 mM EDTA (pH 7.5) and 100 µM NADPH, and mixed with 40 nM human thioredoxin reductase. Absorbance at 340 nm was measured and corrected against the blank value (with the same amounts of enzyme, but without compound A). The same experiments using 50 µm (●) and 100 µM (Δ) Compound A mixed with 17 nM enzyme were performed.

The reaction was fast since with 50 µM Compound A the reaction was complete after 1 min. It was followed by a very slow decrease in the absorbance at 340 nm demonstrating that compound A was not redox cycling with oxygen in contrast to other selenium compounds like selenite or selenocystine. When 6 M guanidine hydrochloride containing DTNB was added to the cuvette at 7 min, an absorbance at 412 nm of 0.400 was measured indicating formation of selenol groups. Compound A itself gave no reaction with DTNB. The reaction with 100 μM compound A was seemingly slower from the decrease in absorbance at 340 nm using 40 nM enzyme.

Figure 2:
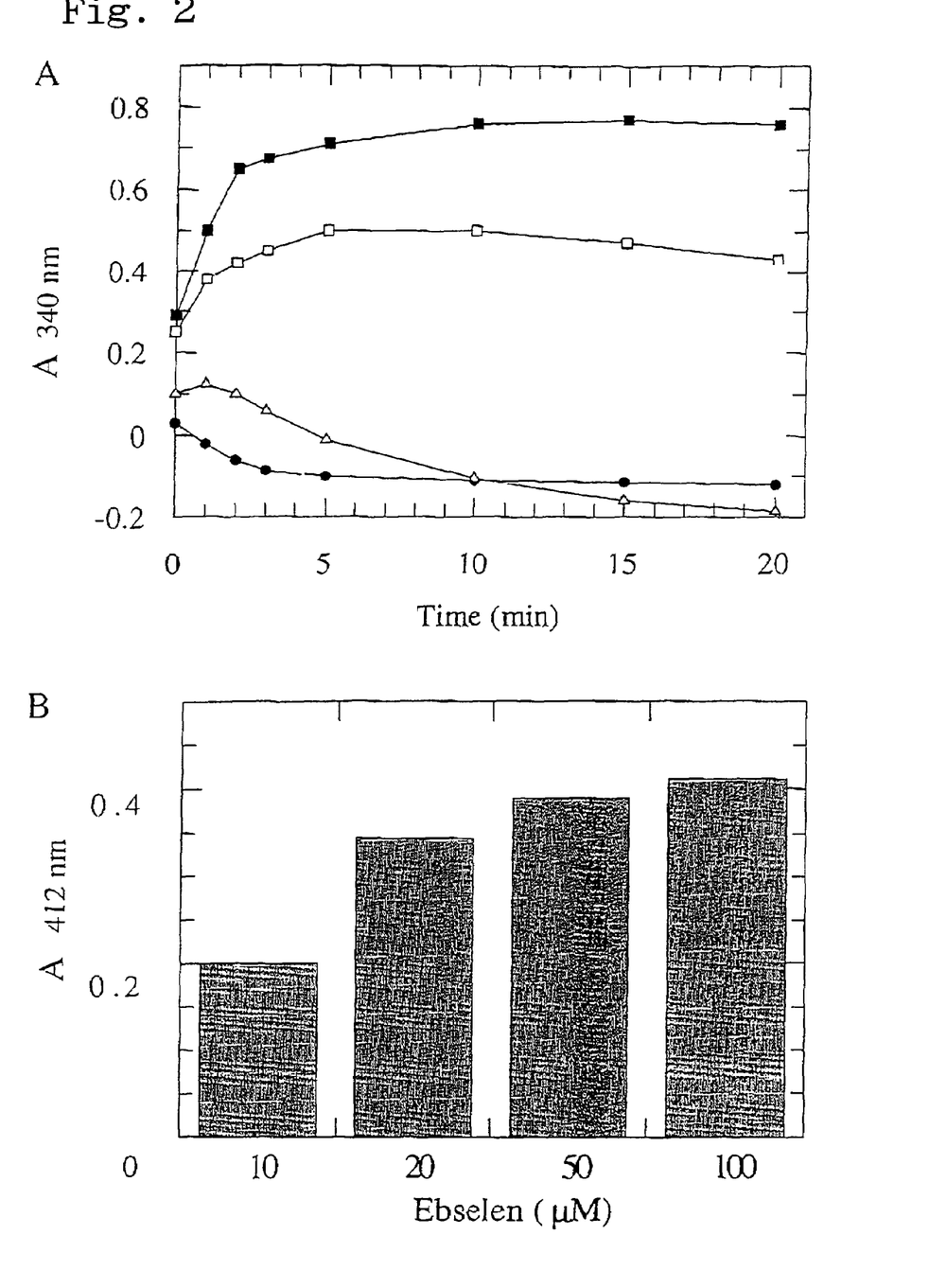
FIG. 2 depicts reduction of compound A by thioredoxin reductase. (A) shows reduction of compound A with a low concentration of thioredoxin reductase, and (B) shows generation of selenol groups detected by DTNB after reduction of Compound A by thioredoxin reductase for 10 min. In the figures, Ebselen means compound A.

A number of experiments with lower concentrations of the enzyme showed a complex change in the absorbance at 340 nm as also seen for 17 nM enzyme and 100 μM compound A (FIG. 1). After an initial decrease, an increase in the absorbance at 340 nm was observed followed by a decrease to give the same value after 15 min as in the sample added with 40 nM enzyme. The result with 7.5 nM enzyme is illustrated in FIG. 2 using 10, 20 50 and 100 μM Compound A. FIG. 2A shows reduction of compound A with a low concentration of thioredoxin reductase. Cuvettes contained 0.55 ml of a solution containing 50 mM Tris-Cl, 1 mM EDTA (pH 7.5), 100 μM NADPH, and 10 μM (●), 20 μM (∆), 50 μM (□) or 100 μM (■) Compound A. Each 7.5 nM TrxR was added to the four sample cuvettes. A blank without Compound A at time zero resulted in a decrease in absorbance at 340 nm indicating oxidation of NADPH with 10 μM Compound A. The cuvettes with 50 and 100 μM Compound A showed an increase in absorbance at 340 nm and visible precipitation masked the oxidation of NADPH.

FIG. 2B shows generation of selenol groups detected by DTNB after reduction of Compound A by thioredoxin reductase for 10 min. The same experiment as in FIG. 2A above was repeated for 10 min. Reactions were stopped by addition of 0.5 ml of 6 M guanidine-HCl, 0.20 M Tris-Cl, pH 8.0, 1 mM DTNB, and absorbance at 412 nm was determined and a background of the blank was cancelled to measure selenol groups. The highest concentrations of compound A (50 and 100 μM) gave visible precipitates in the cuvettes. When reactions were stopped by 6 M guanidine hydrochloride and DTNB, all cuvettes contained selenol-like material (FIG. 2B). Apparently, the precipitation masks the decrease in the absorbance at 340 nm resulting from NADPH oxidation and reduction of compound A to the selenol.

Reduction of compound A by NADPH and the enzyme will produce the selenol via an isoselenazolone ring-opened bound intermediate (the following scheme).

Reaction of this intermediate with compound A or reaction of compound A with an enzyme bound intermediate should then produce the diselenide, which has a lower solubility giving rise to the precipitate and increase in absorbance at 340 nm. The diselenide was also reduced to the selenol since addition of 40 nM enzyme to a cuvette with 100 μM compound A and precipitate containing only 4 nM enzyme rapidly cleared the solution and gave the final NADPH oxidation recorded as a variation of the absorbance at 340 nm. The formation of the insoluble diselenide was not a unique feature of the enzyme since it could be mimicked by using a low non-stoichiometric concentration of DTT (10 μM) and 100 μM compound A, whereas excess DTT only gave the selenol as also shown by HPLC.

To determine the $K_m$- and $V_{max}$ values for compound A, 15 nM enzyme was used with 5, 10 and 20 μM compound A. After 30 seconds, the 5 μM of NADPH was oxidized in all cuvettes, followed by slow increase of the compound A concentrations which may represent diselenide reduction. A $K_m$-value for compound A below 5 μM was evident and a $K_{cat}$ of 1000±300/min was calculated. This makes compound A a substrate of unusual efficiency since human Trx-$S_2$ has a $K_m$-value of 2.5 μM and a $K_{cat}$ of 3000/min.

(b) Effects of Compound A on the Enzymatic Activity of the Mammalian Thioredoxin System To test whether or not Compound A inhibited thioredoxin reductase, enzyme assays were performed. No inhibition was observed with DTNB as substrate using 50 μM Compound A and 10 nM enzyme and only a small effect was seen in an insulin disulfide reduction assay using thioredoxin and thioredoxin reductase (Table 1). The later effect should come from competition with Trx in the assay since compound A did not catalyze insulin disulfide reduction together with the enzyme. Preincubation of the enzyme with compound A in the presence or absence of NADPH did not inhibit the enzyme.

Table 1 shows the effect of compound A on the enzymatic activity of mammalian thioredoxin reductase. (A) shows the result of reactions when mixing 100 nM potassium phosphate (pH 7), 2 mM EDTA, 0.2 mM NADPH, 0.16 mM insulin, 5 μM human Trx and indicated amounts of compound A. The reactions were started by addition of 10 nM calf thymus thioredoxin reductase in the total volume of 0.55 ml of the mixture, and the absorbance at 340 nm was followed for 3 min at 20° C. Then 0.5 ml of a mixture containing 6 M guranidine

HCl, 0.20 M Tris-HCl (pH 8.0) and 1 mM DTNB was added to stop the reaction and the absorbance at 412 nm was used to calculate the amount of SH-groups generated in insulin. In (B), 10 nM calf thymus thioredoxin reductase was preincubated with or without 50 µM compound A and 100 µM NADPH for 1 h. Then 10 µl of the resulting solution was added to 500 µl of a mixture of 0.1 M Tris-HCl (pH 8.0), 1 mM EDTA and 5 mM DTNB to determine activity at 412 nm. Activity is expressed as the amount of SH-groups generated (µM) after 3 min.

TABLE 1

| Compound A (µM) | (A) Trx-catalyzed insulin disulfide reduction | | | (B) Reduction of DTNB | |
|---|---|---|---|---|---|
| | 0 | 5 | 10 | 0 | 50 |
| SH-group (µM) | 79.8 | 70.6 | 68.4 | 7.3 | 7.5 |
| Activity (%) | 100 | 89 | 88 | 100 | 103 |

(3) Effect of Thioredoxin on Compound A Reduction

Figure 3:
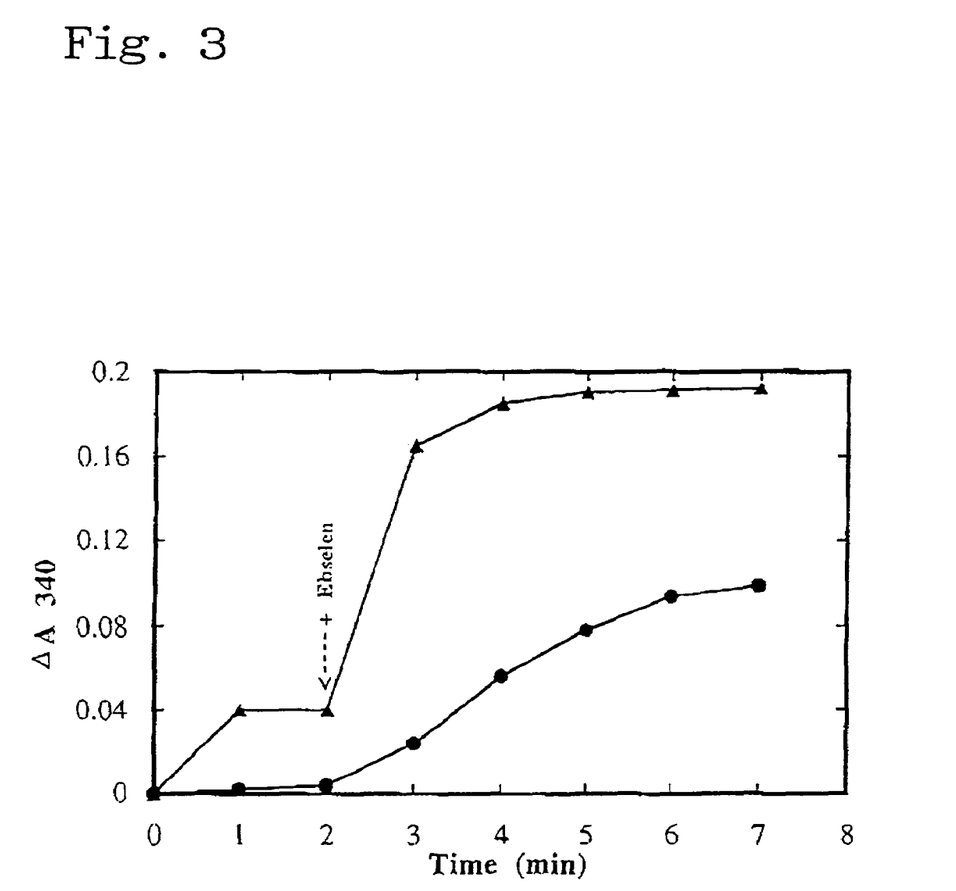
FIG. 3 shows effect of human thioredoxin on reduction of compound A by thioredoxin reductase.

Addition of human thioredoxin to thioredoxin reductase, NADPH and Compound A increased the reaction rate. FIG. 3 shows the effect of human thioredoxin on reduction of Compound A by thioredoxin reductase. The oxidation of NADPH by 10 nM TrxR was recorded in the presence of no ( )or 5 µM (♦) of human Trx-$S_2$ in 0.5 ml of a mixture containing 50 mM Tris-HCl, 1 mM EDTA (pH 7.5) and 100 µM NADPH. During the first 2 min Trx-$S_2$ was reduced to Trx-$(SH)_2$. At the arrow compound A was added to both cuvettes. The result demonstrates that Trx-$(SH)_2$ is a fast reductant of Compound A according to the following reaction formulae.

Trx-$(SH)_2$+Compound A→Trx-$S_2$+Compound A/selenol

Figure 4:
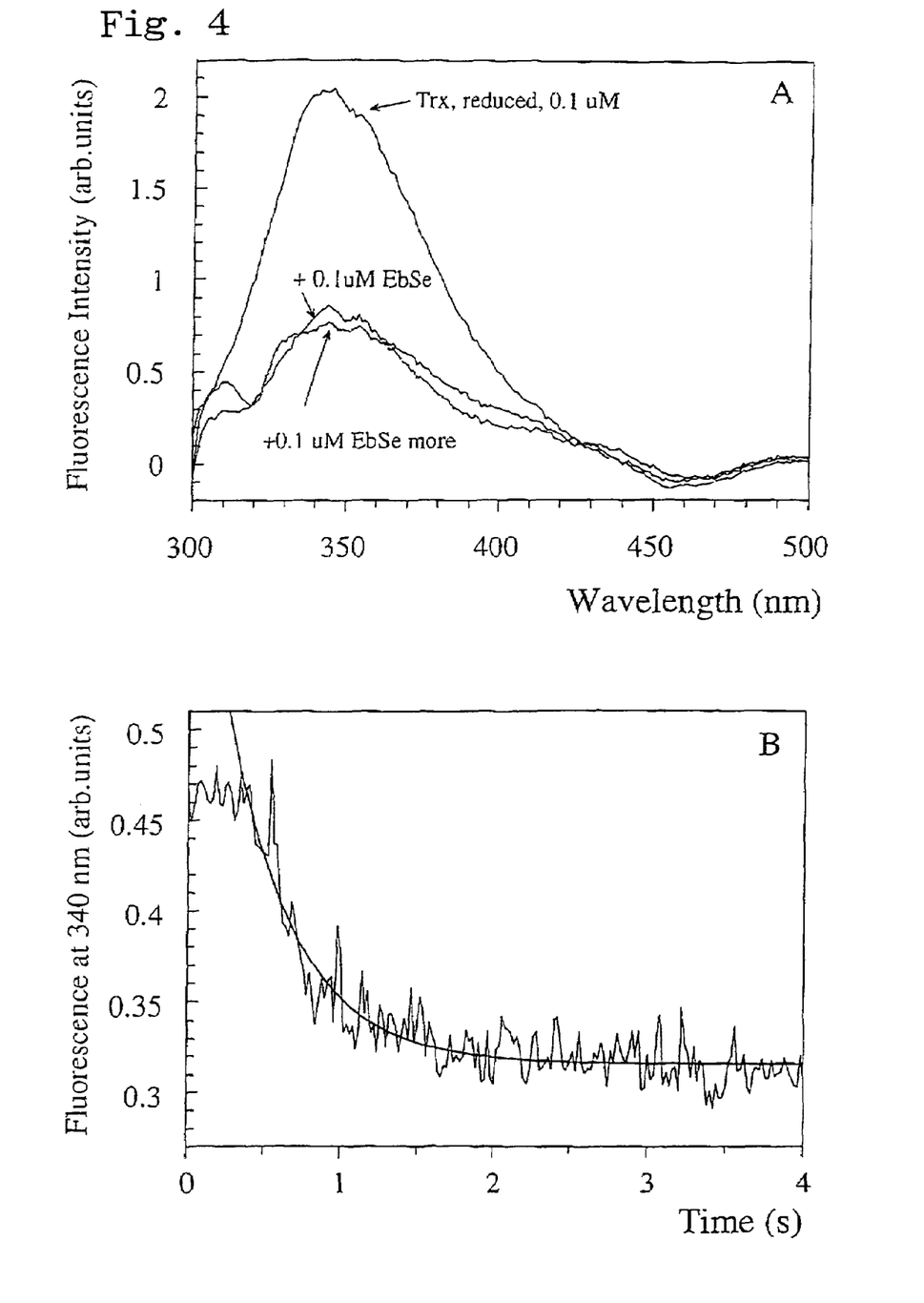
FIG. 4 depicts oxidation of E.coli Trx-(SH)$_2$ by compound A determined by fluorescence spectroscopy (FIG.4 (A)), and the decreasing ratio of the fluorescence emission at 340 nm following the mixing of 0.1 µM Trx-(SH)$_2$ and 0.1 µM compound A (FIG.4 (B)),. In the figures, Trx represents thioredoxin and Ebse compound A.

Trx-$S_2$+NADPH+$H^+$→TrxR→Trx-$(SH)_2$+$NADP^+$ (4) Reaction of Compound A with *E.coli* Trx-$(SH)_2$ Mammalian and *E.coli* Trx have the same active site GPC and reactivity with disulfides. Since *E.coli* Trx-$(SH)_2$ has a 3-fold higher tryprophan fluorescence than Trx-$S_2$, this substance was used to trace the reaction with Compound A. The spectral changes in 0.1 µM Trx-$(SH)_2$ by mixing with 0.1 µM compound A showed oxidation to Trx-$S_2$. FIG. 4A shows oxidation of *E.coli* Trx-$(SH)_2$ by compound A determined by fluorescence spectroscopy. $N_2$ equilibrated 0.1 M potassium phosphate was added with 0.1 µM (1.2 µg/ml) of *E.coli* Trx-$(SH)_2$ and then with 1 mM EDTA (pH 7.5) to prepare a sample. Fluorescence of the sample was excited at 290 nm. The absorbance at the wavelength range from 300 to 500 nm was recorded. Then 0.1 µM of compound A was added and a spectrum was recorded. FIG. 4B shows the decreasing ratio of the fluorescence emission at 340 nm following the mixing of 0.1 µM Trx-$(SH)_2$ and 0.1 µM compound A. The relative fluorescence emission for 0.1 µM Trx-$(SH)_2$ changed in the deadtime of mixing with 0.1 µM of compound A, indicating an oxidation rate faster than $2 \times 10^7$ $M^{-1}s^{-1}$ of Trx-$(SH)_2$. This is the fastest reaction for oxidation of reduced thioedoxin by a low molecular weight compound.

Figure 5:
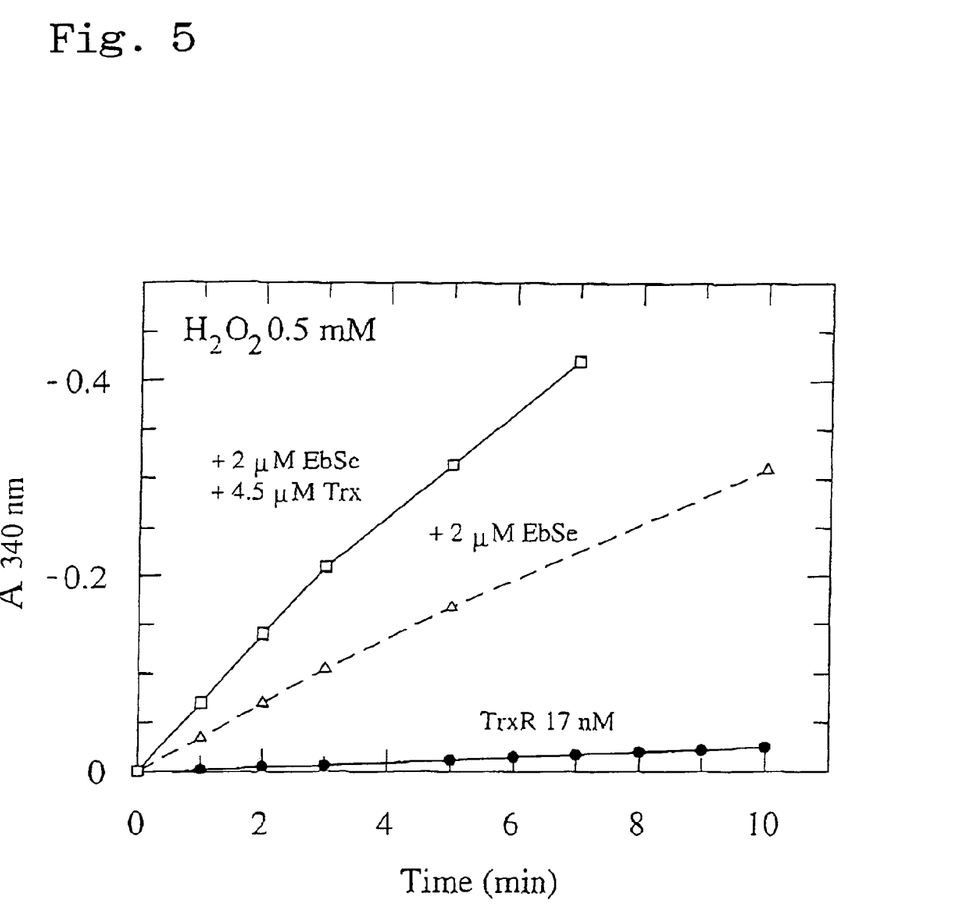
FIG. 5 shows reduction of hydrogen peroxide by human thioredoxin reductase and effect of compound A and thioredoxin. In the figure, Trx, EbSe and TrxR represent thioredoxin, compound A and thioredoxin reductase, respectively.

(5) Stimulation of the Hydrogen Peroxide Reductase Activity of Thioredoxin Reductase by Compound A Mammalian thioredoxin reductase directly reduced hydrogen peroxide. FIG. 5 shows reduction of hydrogen peroxide by human thioredoxin reductase and effect of Compound A and thioredoxin. To cuvettes containing 50 mM Tris-HCl, 1 mM EDTA (pH 7.5) and 100 µM NADPH was added 0.5 mM hydrogen peroxide and 17 nM human TrxR ( ), 17 nM human TrxR plus 2 µM compound A (Δ) or 17 nM human TrxR plus 2 µM Compound A and 4.5 µM human Trx (□). The absorbance at 340 nm was determined against a blank with 17 nM thioredoxin reductase but without hydrogen peroxide. As a result, with 0.50 mM hydroperoxide a turnover number of $30 \times min^{-1}$ was calculated. Addition of 2 µM compound A stimulated the activity with the enzyme which increased its activity to a turnover of $450 \times min^{-1}$ or 15-fold. Additional 4.5 µm human Trx increased the activity to a turnover of $900 \times min^{-1}$ or 30-fold. Thus, Compound A acts to dramatically increase the hydrogen peroxide reductase activity of thioredoxin reductase and also acts as a thioredoxin peroxidase mimic.

Figure 6:
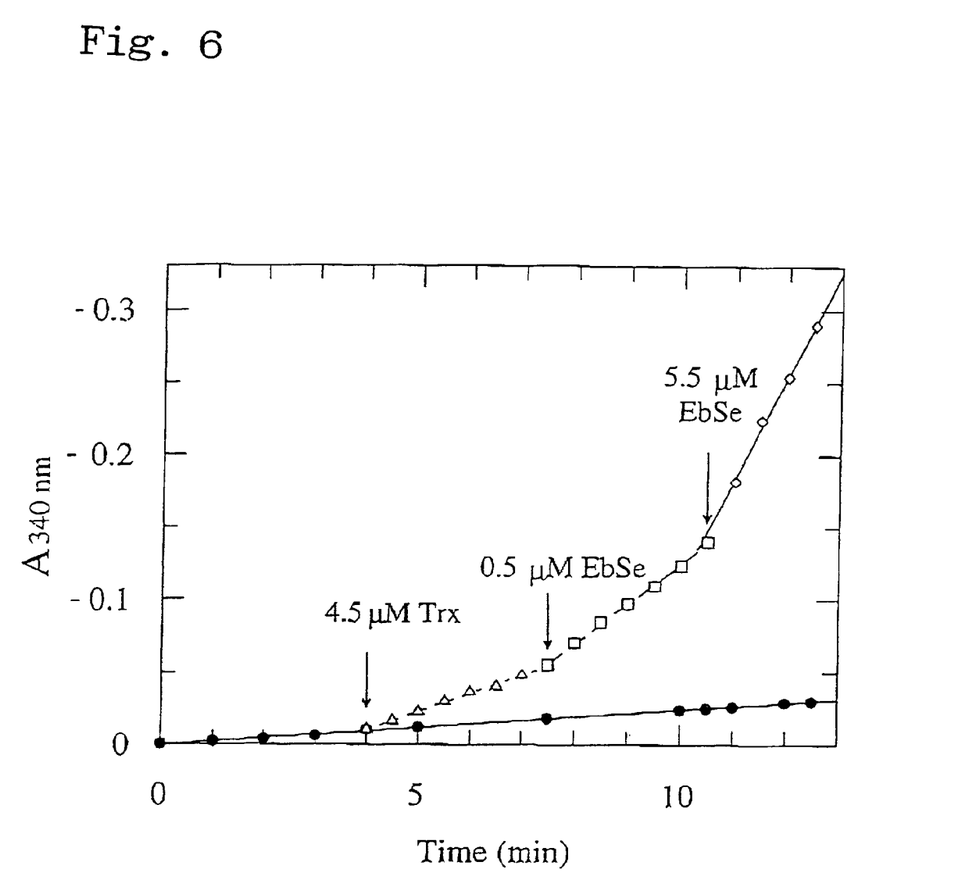
FIG. 6 shows effect of thioredoxin and compound A on reduction of hydrogen peroxide by thioredoxin reductase. In the figure, Trx represents thioredoxin and EbSe compound A.

(6) Effects of Compound A and Thioredoxin at High Concentration Hydrogen Peroxide Addition of 4.5 µM thioredoxin to 17 nM thioredoxin reductase stimulated the reduction of hydrogen peroxide. FIG. 6 shows effect of thioredoxin and Compound A on reduction of hydrogen peroxide by thioredoxin reductase. The same conditions as in FIG. 5 were applied with only 17 nM thioredoxin reductase (●) and addition of 4.5 µM Trx (Δ). Then 0.5 µM compound A was added to adjust the final compound A concentration to 5.5 µM. Compound A at a low concentration (0.5 µM) increased the reaction rate and 5.5 µM compound A stimulated strongly. Using hydrogen peroxide (2 mM), TrxR (17 nM) and human Trx (5 µM), the same rate or 23 µM $min^{-1}$ of the NADPH oxidation rate was obtained by 1, 2 and 5 µM compound A. Thus, under these conditions the enzyme turnover was 1328 $min^{-1}$ and that of 1 nM Compound A $23 \times min^{-1}$ demonstrating a highly efficient peroxidase system.

(7) Effects at Low Hydrogen Peroxide Concentration

Figure 7:
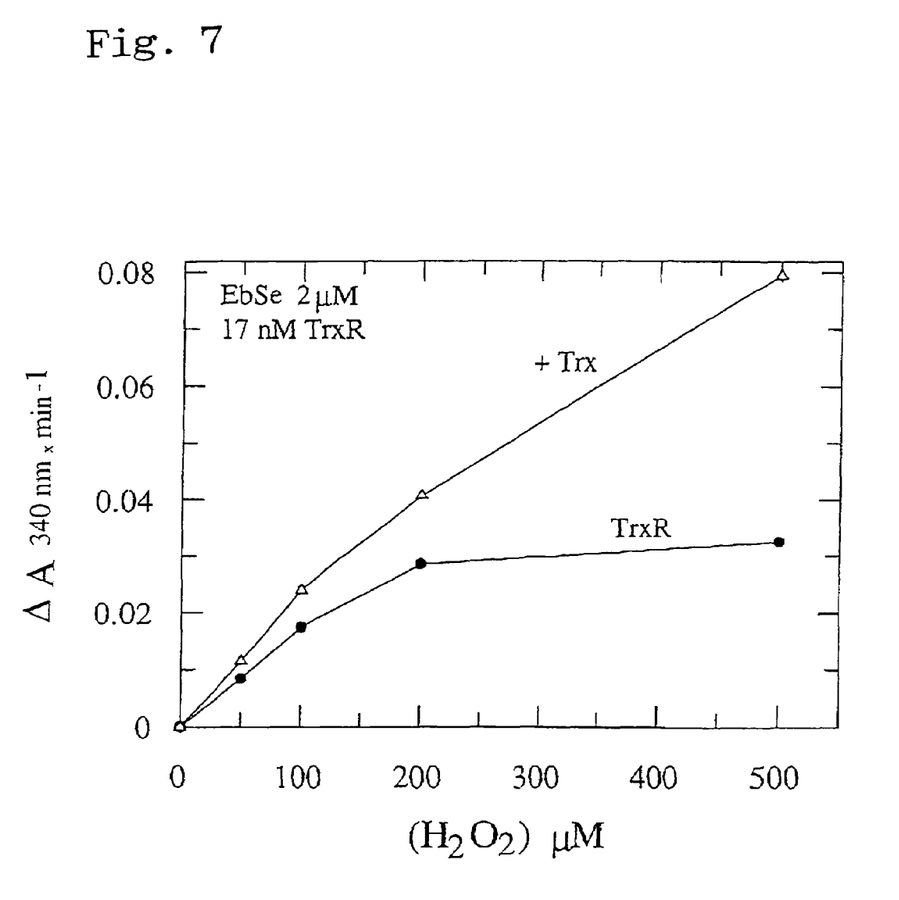
FIG. 7 shows effect of hydrogen peroxide concentrations on activity of thioredoxin with compound A. In the figure, Trx, TrxR and EbSe represent thioredoxin, thioredoxin reductase and compound A, respectively.
Figure 8:
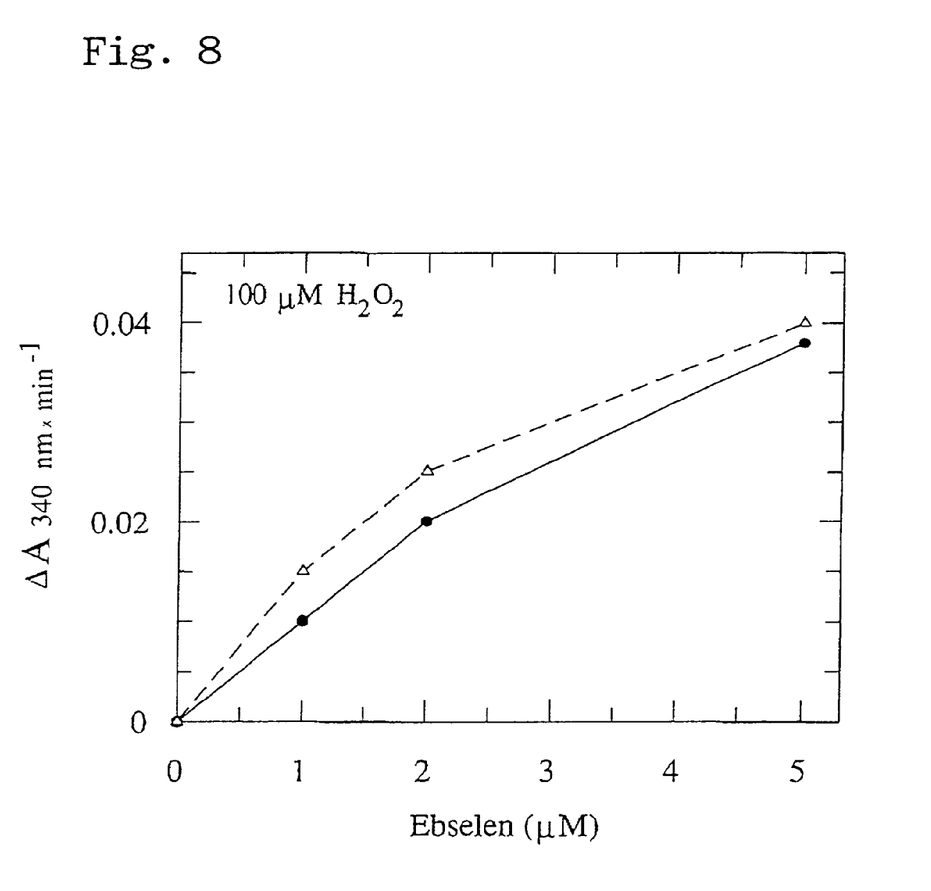
FIG. 8 shows effects of compound A on reduction of hydrogen peroxide. In the figure, Ebselen means compound A.

With 2 µM Compound A only 17 nM thioredoxin reductase showed a high activity with 100 µM hydrogen peroxide. FIG. 7 shows effect of hydrogen peroxide concentrations on activity of TrxR with compound A. Determination was performed using 17 nM human thioredoxin reductase and 2 µM compound A (●) or with 17 nM human thioredoxin reductase plus 4.5 µM Trx and 2 µM compound A (Δ) with the indicated concentrations of hydrogen peroxide. Thus compound A increased activity of the enzyme with lower more physiologically relevant concentrations, and this increase was about 25-fold. FIG. 8 shows effects of compound A on reduction of 100 µm hydrogen peroxide using only 10 nM thioredoxin reductase ( )or 10 nM thioredoxin reductase +4.5 µM human Trx (Δ). Activity is expressed as the variation ratio per min, $\Delta A_{340}/min$. The thioredoxin-dependent reaction still increased, and 100 µM hydrogen peroxide and 1, 2 and 5 µM compound A stimulated the reaction in a similar way both with and without Trx.

INDUSTRIAL APPLICABILITY

The substrate for thioredoxin reductase of the present invention can activate the thioredoxin/thioredoxin reductase system, in particular, the substrate can enhance peroxidase activity proceeded by thioredoxin reductase. Accordingly, the substrate is very useful as various agents, for example, as an antioxidant which prevents peroxidation of a substance in vivo by oxidizing reduced thioredoxin in the peroxidase reaction of thioredoxin reductase.

What is claimed is:

1. A method for reduction of a substrate with thioredoxin reductase, comprising combining the thioredoxin reductase, the substrate and NADPH in an in vitro composition, wherein the composition does not include insulin, under conditions to reduce the substrate, the substrate comprising a substance selected from the group consisting of a compound represented by the following general formula (1) or (1') and a physiologically acceptable salt thereof:

(1)

(1')

wherein $R^1$ and $R^2$ independently represent a hydrogen atom, a halogen atom, a trifluoromethyl group, a nitro group, a $C_1$-$C_6$ alkyl group, or a $C_1$-$C_6$ alkoxyl group, or $R^1$ and $R^2$ may combine together to represent methylenedioxy group; $R^3$ represents an aryl group, an aromatic heterocyclic group, a 5- to 7-membered cycloalkyl group, or a 5- to 7-membered cycloalkenyl group, and the aryl group, the aromatic heterocyclic group, the cycloalkyl group, and the cycloalkenyl group may be substituted with one or more substituents; $R^4$ represents a hydrogen atom, a hydroxyl group, a —S-glutathione group, a —S-α-amino acid group, or an aralkyl group whose aryl moiety may be substituted with one or more substituents; $R^5$ represents a hydrogen atom or a $C_1$-$C_6$ alkyl group, or $R^4$ and $R^5$ may combine together to represent single bond; Y represents oxygen atom or sulfur atom; n represents an integer of from 0 to 5; and the selenium atom may be oxidized.

2. The method according to claim 1 wherein the substrate comprises a substance selected from the group consisting of 2-phenyl-1,2-benziso-selenazol-3(2H)-one or a ring-opened form thereof and a physiologically acceptable salt thereof.

3. A method of enhancing peroxidase activity of thioredoxin reductase, comprising combining NAPDH, thioredoxin reductase, thioredoxin and a substrate in an in vitro composition, wherein the composition does not include insulin, under conditions to enhance peroxidase activity of thioredoxin reductase, the substrate comprising a substance selected from the group consisting of a compound represented by the following general formula (1) or (1') and a physiologically acceptable salt thereof:

(1)

(1')

wherein $R^1$ and $R^2$ independently represent a hydrogen atom, a halogen atom, a trifluoromethyl group, a nitro group, a $C_1$-$C_6$ alkyl group, or a $C_1$-$C_6$ alkoxyl group, or $R^1$ and $R^2$ may combine together to represent methylenedioxy group; $R^3$ represents an aryl group, an aromatic heterocyclic group, a 5- to 7-membered cycloalkyl group, or a 5- to 7-membered cycloalkenyl group, and the aryl group, the aromatic heterocyclic group, the cycloalkyl group, and the cycloalkenyl group may be substituted with one or more substituents; $R^4$ represents a hydrogen atom, a hydroxyl group, a —S-glutathione group, a —S-α-amino acid group, or an aralkyl group whose aryl moiety may be substituted with one or more substituents; $R^5$ represents a hydrogen atom or a $C_1$-$C_6$ alkyl group, or $R^4$ and $R^5$ may combine together to represent single bond; Y represents oxygen atom or sulfur atom; n represents an integer of from 0 to 5; and the selenium atom may be oxidized.

4. The method according to claim 3 wherein the substrate comprises a substance selected from the group consisting of 2-phenyl-1,2-benzisoselenazol-3(2H)-one or a ring-opened form thereof and a physiologically acceptable salt thereof.

5. A method of oxidizing reduced thioredoxin by a substrate, the method comprising combining reduced thioredoxin and a substrate in an in vitro composition, wherein the composition does not include insulin, under conditions to oxidize the reduced thioredoxin with the substrate, the substrate comprising a substance selected from the group consisting of a compound represented by the following general formula (1) or (1') and a physiologically acceptable salt thereof:

(1)

(1')

wherein $R^1$ and $R^2$ independently represent a hydrogen atom, a halogen atom, a trifluoromethyl group, a nitro group, a $C_1$-$C_6$ alkyl group, or a $C_1$-$C_6$ alkoxyl group, or $R^1$ and $R^2$ may combine together to represent methylenedioxy group; $R^3$ represents an aryl group, an aromatic heterocyclic group, a 5- to 7-membered cycloalkyl group, or a 5- to 7-membered cycloalkenyl group, and the aryl group, the aromatic heterocyclic group, the cycloalkyl group, and the cycloalkenyl group may be substituted with one or more substituents; $R^4$ represents a hydrogen atom, a hydroxyl group, a —S-glutathione group, a —S-α-amino acid group, or an aralkyl group whose aryl moiety may be substituted with one or more substituents; $R^5$ represents a hydrogen atom or a $C_1$-$C_6$ alkyl group, or $R^4$ and $R^5$ may combine together to represent single bond; Y represents oxygen atom or sulfur atom; n represents an integer of from 0 to 5; and the selenium atom may be oxidized.

6. A method for reducing a peroxide comprising combining thioredoxin, thioredoxin reductase, NAPDH and a substrate in an in vitro composition, wherein the composition does not include insulin, under conditions to reduce the peroxide, the substrate comprising a substance selected from the group consisting of a compound represented by the following general formula (1) or (1') and a physiologically acceptable salt thereof:

(1)

(1')

wherein $R^1$ and $R^2$ independently represent a hydrogen atom, a halogen atom, a trifluoromethyl group, a nitro group, a $C_1$-$C_6$ alkyl group, or a $C_1$-$C_6$ alkoxyl group, or $R^1$ and $R^2$ may combine together to represent methylenedioxy group; $R^3$ represents an aryl group, an aromatic heterocyclic group, a 5- to 7-membered cycloalkyl group, or a 5- to 7-membered cycloalkenyl group, and the aryl group, the aromatic heterocyclic group, the cycloalkyl group, and the cycloalkenyl group may be substituted with one or more substituents; $R^4$ represents a hydrogen atom, a hydroxyl group, a —S-glutathione group, a —S-α-amino acid group, or an aralkyl group whose aryl moiety may be substituted with one or more substituents; $R^5$ represents a hydrogen atom or a $C_1$-$C_6$ alkyl group, or $R^4$ and $R^5$ may combine together to represent single bond; Y represents oxygen atom or sulfur atom; n represents an integer of from 0 to 5; and the selenium atom may be oxidized.

7. A method of preventing peroxidation of a substrate comprising combining thioredoxin, thioredoxin reductase and NADPH with a substrate in an in vitro composition, wherein the composition does not include insulin, under conditions to prevent peroxidation of the substrate, the substrate being selected from the group consisting of a compound represented by the following general formula (1) or (1') and a physiologically acceptable salt thereof:

(1)

(1')

wherein $R^1$ and $R^2$ independently represent a hydrogen atom, a halogen atom, a trifluoromethyl group, a nitro group, a $C_1$-$C_6$ alkyl group, or a $C_1$-$C_6$ alkoxyl group, or $R^1$ and $R^2$ may combine together to represent methylenedioxy group; $R^3$ represents an aryl group, an aromatic heterocyclic group, a 5- to 7-membered cycloalkyl group, or a 5- to 7-membered cycloalkenyl group, and the aryl group, the aromatic heterocyclic group, the cycloalkyl group, and the cycloalkenyl group may be substituted with one or more substituents; $R^4$ represents a hydrogen atom, a hydroxyl group, a —S-glutathione group, a —S-α-amino acid group, or an aralkyl group whose aryl moiety may be substituted with one or more substituents; $R^5$ represents a hydrogen atom or a $C_1$-$C_6$ alkyl group, or $R^4$ and $R^5$ may combine together to represent single bond; Y represents oxygen atom or sulfur atom; n represents an integer of from 0 to 5; and the selenium atom may be oxidized.

8. The method according to claim 5 wherein the substrate comprises a substance selected from the group consisting of 2-phenyl-1,2-benziso-selenazol-3(2H)-one or a ring-opened form thereof and a physiologically acceptable salt thereof.

9. The method according to claim 6 wherein the substrate comprises a substance selected from the group consisting of 2-phenyl-1,2-benziso-selenazol-3(2H)-one or a ring-opened form thereof and a physiologically acceptable salt thereof.

10. The method according to claim 7 wherein the substrate comprises a substance selected from the group consisting of 2-phenyl-1,2-benziso-selenazol-3(2H)-one or a ring-opened form thereof and a physiologically acceptable salt thereof.

* * * * *